United States Patent
Sasaki et al.

(10) Patent No.: US 10,448,908 B2
(45) Date of Patent: Oct. 22, 2019

(54) RADIOGRAPHIC IMAGING APPARATUS AND IMAGING SYSTEM

(71) Applicant: CANON KABUSHIKI KAISHA, Tokyo (JP)

(72) Inventors: Yoshito Sasaki, Kumagaya (JP); Shoshiro Saruta, Kodama-gun (JP); Takamasa Ishii, Honjo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 572 days.

(21) Appl. No.: 14/871,198

(22) Filed: Sep. 30, 2015

(65) Prior Publication Data

US 2016/0097865 A1    Apr. 7, 2016

(30) Foreign Application Priority Data

Oct. 7, 2014 (JP) .................. 2014-206681

(51) Int. Cl.
  *A61B 6/00* (2006.01)
  *G01T 1/20* (2006.01)
  *G01T 1/24* (2006.01)

(52) U.S. Cl.
  CPC .......... *A61B 6/4233* (2013.01); *A61B 6/4208* (2013.01); *G01T 1/2018* (2013.01); *G01T 1/24* (2013.01)

(58) Field of Classification Search
  CPC ... A61B 6/4208; A61B 6/4233; G01T 1/2018; G01T 1/24

(Continued)

(56) References Cited

U.S. PATENT DOCUMENTS 5,594,253 A * 1/1997 Bueno ............... G01T 1/201
                                                    250/367
5,636,299 A * 6/1997 Bueno ............... G01T 1/201
                                                    250/367

(Continued)

FOREIGN PATENT DOCUMENTS

JP    2002-22835 A    1/2002
JP    2002-202373 A   7/2002

(Continued)

OTHER PUBLICATIONS

Office Action dated Aug. 21, 2018, in counterpart application JP 2014-206681 (11 pages).

*Primary Examiner* — Allen C. Ho
(74) *Attorney, Agent, or Firm* — Venable LLP

(57) ABSTRACT

Provided is a radiographic imaging apparatus that is high in sharpness of a picked up image and excellent in DQE by improving the amount of light that enters a photoelectric conversion element, despite a scintillator layer being formed thick. The radiographic imaging apparatus includes: the photoelectric conversion element; and a wavelength converting layer which has a bottom surface located above the photoelectric conversion element and a top surface for receiving an incident radiation ray, and which contains a scintillator layer. The wavelength converting layer has light transmitting properties in at least a region positioned to be above the photoelectric conversion element, and contains the scintillator layer at a density that is lower on the bottom surface side than on the top surface side in the thickness direction of the region.

6 Claims, 7 Drawing Sheets

(58) Field of Classification Search
USPC .............................. 378/19, 98.8; 250/370.09
See application file for complete search history.

(56) References Cited

U.S. PATENT DOCUMENTS

| | | | | |
|---|---|---|---|---|
| 5,712,483 A * | 1/1998 | Boone | ............... | G01T 1/1645 250/367 |
| 5,821,541 A * | 10/1998 | Tümer | ............... | G01T 1/006 250/370.09 |
| 5,933,473 A * | 8/1999 | Kitaguchi | ............... | G01N 23/043 378/149 |
| 6,167,110 A * | 12/2000 | Possin | ............... | G01T 1/201 250/370.11 |
| 6,353,227 B1 * | 3/2002 | Boxen | ............... | G21K 1/025 250/363.06 |
| 6,519,313 B2 * | 2/2003 | Venkataramani | ..... | G01T 1/2018 250/367 |
| 7,075,104 B2 * | 7/2006 | Faris | ............... | B81C 1/00071 250/370.01 |
| 7,115,876 B2 * | 10/2006 | Ren | ............... | G01T 1/1644 250/366 |
| 7,252,789 B2 * | 8/2007 | Venkataramani | .. | C09K 11/7774 250/363.03 |
| 7,315,027 B2 * | 1/2008 | Okada | ............... | G01T 1/2018 250/370.11 |
| 7,323,692 B2 * | 1/2008 | Rowlands | ............... | G01T 1/2018 250/370.09 |
| 7,426,258 B1 * | 9/2008 | Zweig | ............... | A61B 6/12 378/98.3 |
| 7,538,330 B2 * | 5/2009 | Nomura | ............... | G01T 1/2018 250/367 |
| 7,547,895 B2 * | 6/2009 | Manivannan | ............... | C09K 11/02 250/358.1 |
| 7,577,233 B1 * | 8/2009 | Tsang | ............... | G01N 23/223 378/207 |
| 7,586,252 B2 * | 9/2009 | Bueno | ............... | C09K 11/613 250/370.09 |
| 7,625,502 B2 * | 12/2009 | Clothier | ............... | B82Y 30/00 252/301.4 H |
| 7,635,848 B2 * | 12/2009 | Nelson | ............... | G01T 1/2002 250/370.11 |
| 7,696,481 B2 * | 4/2010 | Tkaczyk | ............... | G01T 1/2018 250/363.02 |
| 7,723,693 B2 * | 5/2010 | Okada | ............... | G01T 1/2018 250/370.01 |
| 7,772,562 B2 * | 8/2010 | Yamagishi | ............... | G01T 1/2018 250/370.11 |
| 8,049,177 B2 * | 11/2011 | Sato | ............... | G01T 1/2018 250/367 |
| 8,063,379 B2 * | 11/2011 | Suhami | ............... | G01T 5/02 250/370.09 |
| 8,304,736 B2 * | 11/2012 | Gagnon | ............... | G01T 1/2018 250/362 |
| 8,338,790 B2 * | 12/2012 | Levene | ............... | G01T 1/2018 250/367 |
| 8,409,908 B2 * | 4/2013 | Li | ............... | A61B 6/032 257/443 |
| 8,440,975 B2 | 5/2013 | Inoue et al. | | |
| 8,476,593 B2 * | 7/2013 | Degenhardt | ............... | G01T 1/249 250/362 |
| 8,476,594 B2 * | 7/2013 | Frach | ............... | G01T 1/2018 250/363.03 |
| 8,525,121 B2 * | 9/2013 | Nakatsugawa | ......... | G01T 1/242 250/367 |
| 8,614,420 B2 * | 12/2013 | Menge | ............... | G01T 1/2008 250/361 R |
| 8,624,194 B2 * | 1/2014 | Ueyama | ............... | H01L 31/115 250/361 R |
| 8,653,465 B2 | 2/2014 | Nagano et al. | | |
| 8,686,369 B2 * | 4/2014 | Reboni | ............... | G03B 42/02 250/366 |
| 8,704,185 B2 | 4/2014 | Ishida et al. | | |
| 8,729,447 B2 * | 5/2014 | Jarron | ............... | H01J 43/246 250/207 |
| 8,735,841 B2 * | 5/2014 | Nakatsugawa | ....... | G01T 1/2018 250/370.11 |
| 8,761,333 B2 * | 6/2014 | Ikhlef | ............... | A61B 6/032 29/428 |
| 8,779,372 B2 * | 7/2014 | Inoue | ............... | G01T 1/2018 250/361 R |
| 8,791,537 B2 * | 7/2014 | Chan | ............... | H01L 31/02322 257/428 |
| 8,962,370 B2 * | 2/2015 | Kawanishi | ............ | H01L 31/115 250/362 |
| 9,006,665 B2 | 4/2015 | Nagano et al. | | |
| 9,040,924 B2 * | 5/2015 | Lewellen | ............... | A61B 6/037 250/361 R |
| 9,064,677 B2 * | 6/2015 | Uchiyama | ............ | H01J 43/246 |
| 9,075,150 B2 * | 7/2015 | Tredwell | ............... | G01T 1/2018 |
| 9,081,104 B2 | 7/2015 | Sawada et al. | | |
| 9,097,808 B2 * | 8/2015 | Hedler | ............... | G01T 1/20 |
| 9,110,174 B2 * | 8/2015 | Wieczorek | ............ | G01T 1/2018 |
| 9,110,176 B2 * | 8/2015 | Oike | ............... | G01T 1/202 |
| 9,116,248 B2 * | 8/2015 | Abenaim | ............... | A61B 6/032 |
| 9,182,504 B2 * | 11/2015 | Nishino | ............... | G01T 1/202 |
| 9,193,903 B2 * | 11/2015 | Hayashi | ............... | A61B 6/03 |
| 9,201,193 B1 * | 12/2015 | Smith | ............... | G02B 6/04 |
| 9,223,035 B2 * | 12/2015 | Isa | ............... | G01T 1/202 |
| 9,229,115 B2 * | 1/2016 | Griesmer | ............... | G01T 1/2018 |
| 9,285,489 B2 * | 3/2016 | Couture | ............... | G01T 1/2018 |
| 9,291,726 B2 * | 3/2016 | Batkilin | ............... | G01T 1/2018 |
| 9,304,211 B2 * | 4/2016 | Goertzen | ............... | G01T 1/2018 |
| 9,315,726 B2 * | 4/2016 | Ronda | ............... | C09K 11/7774 |
| 9,316,750 B2 * | 4/2016 | Hosoi | ............... | G21K 4/00 |
| 9,341,722 B2 * | 5/2016 | Yamazaki | ............ | G01T 1/2018 |
| 9,354,186 B2 * | 5/2016 | Bartolome | ........... | G01N 23/046 |
| 9,354,333 B2 * | 5/2016 | Inoue | ............... | G01T 7/00 |
| 9,360,571 B2 * | 6/2016 | Batkilin | ............... | G01T 1/2018 |
| 9,418,768 B2 * | 8/2016 | Nagata | ............... | G21K 4/00 |
| 9,442,200 B2 * | 9/2016 | Watano | ............... | G01T 1/2018 |
| 9,506,876 B2 * | 11/2016 | Urano | ............... | G01N 23/043 |
| 9,529,095 B2 * | 12/2016 | Kobayashi | ............ | G01T 1/2002 |
| 9,568,614 B2 * | 2/2017 | Ishida | ............... | G01T 1/2006 |
| 9,588,235 B2 * | 3/2017 | Weisfield | ............... | G01T 1/2018 |
| 9,599,726 B2 * | 3/2017 | Xie | ............... | G01T 1/2002 |
| 9,599,728 B2 * | 3/2017 | Levene | ............... | G01T 1/2018 |
| 9,632,185 B2 * | 4/2017 | Kinoshita | ............. | G01T 1/2018 |
| 9,634,057 B2 * | 4/2017 | Racine | ............... | H01L 27/14663 |
| 9,678,222 B2 * | 6/2017 | Snoeren | ............... | G01T 1/2018 |
| 9,684,082 B2 * | 6/2017 | Okamura | ............... | G01T 1/202 |
| 9,696,439 B2 * | 7/2017 | An | ............... | G01T 1/2985 |
| 9,720,100 B2 * | 8/2017 | Habib | ............... | H04N 5/2175 |
| 9,720,106 B2 * | 8/2017 | Horiuchi | ............... | G01T 1/2023 |
| 9,753,152 B2 * | 9/2017 | Wieczorek | ............ | G01T 1/2018 |
| 9,759,821 B2 * | 9/2017 | Noh | ............... | G01T 1/2018 |
| 9,766,353 B2 * | 9/2017 | Kawanishi | ............ | G01T 1/203 |
| 9,770,603 B2 * | 9/2017 | Da Silva Rodrigues | ............... | A61N 5/1071 |
| 9,791,576 B2 * | 10/2017 | Hamano | ............... | G01T 1/2018 |
| 9,810,791 B2 * | 11/2017 | Homma | ............... | G01T 1/2018 |
| 9,835,735 B2 * | 12/2017 | Preston | ............... | G01T 1/02 |
| 9,897,558 B2 * | 2/2018 | Bowdon | ............... | G01N 23/046 |
| 2013/0153775 A1 | 6/2013 | Nomura et al. | | |
| 2013/0168559 A1 | 7/2013 | Saruta et al. | | |
| 2013/0187054 A1 | 7/2013 | Ishii et al. | | |
| 2013/0308755 A1 | 11/2013 | Ishida et al. | | |
| 2013/0341516 A1 | 12/2013 | Ishida et al. | | |
| 2013/0341517 A1 | 12/2013 | Inoue et al. | | |
| 2014/0034836 A1 | 2/2014 | Takei et al. | | |

FOREIGN PATENT DOCUMENTS

| | | | |
|---|---|---|---|
| JP | 2004-150932 A | 5/2004 | |
| JP | 2016-6418 A | 1/2016 | |

* cited by examiner

R ADIOGRAPHIC IMAGING APPARATUS
AND IMAGING SYSTEM

BACKGROUND OF THE INVENTION

Field of the Invention

The present invention relates to a radiographic imaging apparatus and an imaging system.

Description of the Related Art

There have been known radiographic imaging apparatuses that include a scintillator layer for converting radiation into light and a sensor panel with an arrangement of a plurality of photoelectric conversion elements for detecting the light converted from radiation in the scintillator layer. A method of forming a scintillator layer by filling the space between partition walls with scintillator particles is disclosed in Japanese Patent Application Laid-Open No. 2002-202373. This method is superior in that the scintillator layer formed by filling the space between partition walls with scintillator particles yields a picked up image high in sharpness.

Improving the detective quantum efficiency (DQE) in a radiographic imaging apparatus usually requires forming the scintillator layer thick. When the scintillator layer is formed to have a certain thickness or more, light emitted on the radiation incident side is absorbed and scattered by the scintillator in the process of reaching the sensor panel side, thereby attenuating the amount of light. The resultant problem is a reduction in the amount of light entering the photoelectric conversion elements and in the sharpness of a picked up image, which means that DQE is not improved sufficiently.

SUMMARY OF THE INVENTION

The present invention has been made to address the problem described above, and the present invention provides a radiographic imaging apparatus and an imaging system high in sharpness of a picked up image and excellent in DQE by increasing the proportion of light emitted by a thick scintillator layer that enters a photoelectric conversion element formed immediately below the scintillator layer and improving the amount of light that enters the photoelectric conversion element, despite the scintillator layer being formed thick.

According to one embodiment of the present invention, there is provided a radiographic imaging apparatus, including: a photoelectric conversion element; and a wavelength converting layer having a bottom surface located above the photoelectric conversion element, the wavelength converting layer including a scintillator to convert radiation into light, in which the wavelength converting layer has light transmitting properties in at least a region that is positioned to be above the photoelectric conversion element, and the wavelength converting layer includes the scintillator at a density that is lower on the bottom surface side than on a top surface side of the wavelength converting layer opposite from the bottom surface side in a thickness direction of the region.

Further features of the present invention will become apparent from the following description of exemplary embodiments with reference to the attached drawings.

DESCRIPTION OF THE EMBODIMENTS

Exemplary embodiments of the present invention are described in detail below with reference to the drawings.

First Embodiment

A radiographic imaging apparatus is disclosed in a first embodiment of the present invention. A typical example of radiation used for imaging is X-rays. Other radiation than X-rays includes α rays, β rays, and γ rays.

Figure 1:
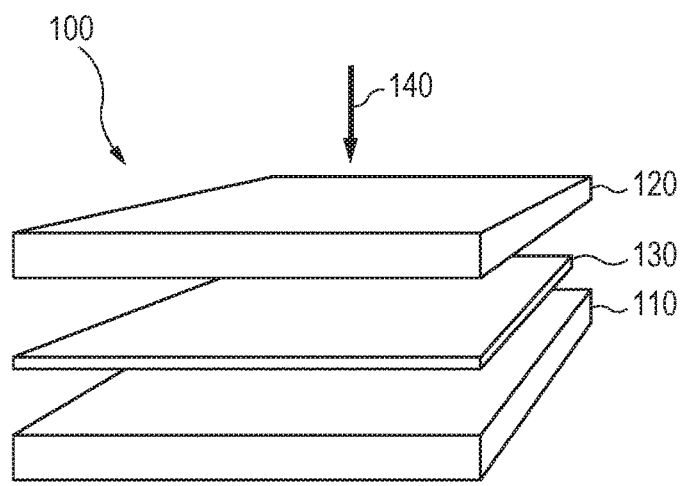
FIG. 1 is a schematic exploded perspective view of a radiographic imaging apparatus.

FIG. 1 is a schematic exploded perspective view of a radiographic imaging apparatus 100 (hereinafter simply referred to as imaging apparatus 100). The imaging apparatus 100 includes a sensor panel 110, a wavelength converting layer (wavelength converting portion) 120, and a bonding member 130, which connects the sensor panel 110 and the wavelength converting layer 120 to each other. The sensor panel 110 includes a sensor array in which a plurality of sensors (photoelectric conversion elements) are arranged in, for example, a matrix pattern. The wavelength converting layer 120 includes a scintillator layer, which contains a scintillator and is configured to convert radiation into light. The bonding member 130 is an adhesive or a viscous material such as silicone, acrylic, or epoxy.

A radiation ray 140, which is represented by the arrow in FIG. 1, travels toward and enters the imaging apparatus 100 to be converted into light in the wavelength converting layer 120. The light from the wavelength converting layer 120 is received by the photoelectric conversion in the sensor panel 110, thereby obtaining electric signals. Based on the electric signals obtained by the sensor panel 110, the imaging apparatus 100 generates radiographic image data in, for example, a signal processing unit (not shown).

Figure 2:
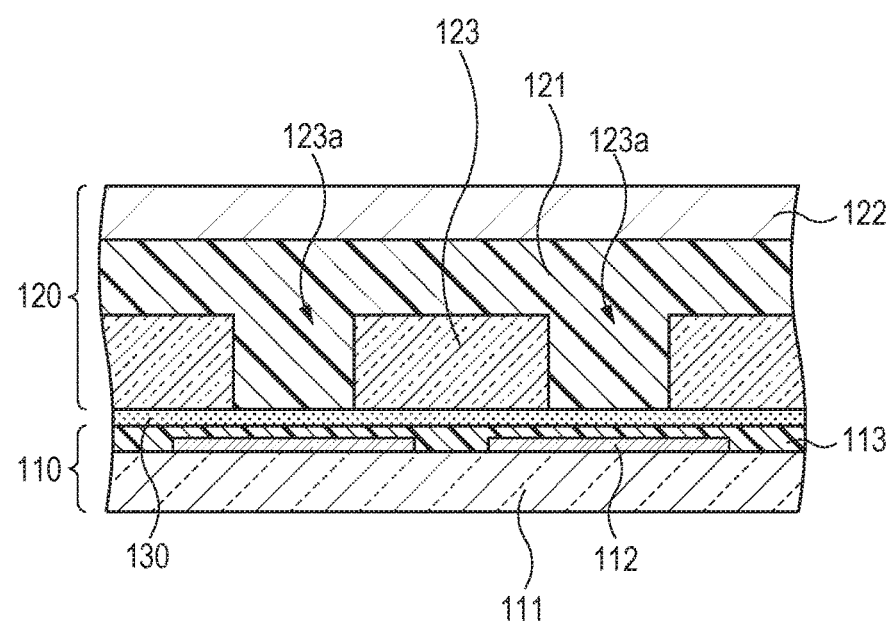
FIG. 2 is a schematic sectional view of the configuration of an imaging apparatus according to a first embodiment of the present invention.

FIG. 2 is a schematic sectional view of the configuration of the imaging apparatus 100 according to this embodiment. The sensor panel 110 in the imaging apparatus 100 includes a sensor substrate 111, a plurality of photoelectric conversion elements 112 formed on the sensor substrate 111, and a protective layer 113 configured to protect the plurality of photoelectric conversion elements 112.

The sensor substrate 111 is an insulating substrate such as a glass substrate, or a semiconductor substrate. When the sensor substrate 111 is an insulating substrate such as a glass substrate, the plurality of photoelectric conversion elements 112 are formed on the sensor substrate 111. When the sensor substrate 111 is a semiconductor substrate, the plurality of photoelectric conversion elements 112 are formed in the sensor substrate 111. A switching element (not shown) is formed next to each photoelectric conversion element 112 in order to read signals based on electric charges that are generated by the photoelectric conversion element 112. The photoelectric conversion element 112 and the switching element constitute a pixel. The pitch between pixels is about 125 µm, for example.

The wavelength converting layer 120 includes a scintillator layer 121, a reflective layer 122 configured to reflect light of the scintillator layer 121, and a structure 123, which is a member having a function of guiding light emitted by the scintillator layer 121 toward the plurality of photoelectric conversion elements 112.

The scintillator layer 121 is a member that contains a scintillator in, for example, a particle form and converts incident radiation into light. Forming the scintillator layer 121 thick improves DQE. The thickness of the scintillator layer 121 is, although varying as appropriate depending on the thickness of the structure 123, approximately 200 µm to approximately 400 µm, for example, 350 µm or so.

The structure 123 is formed from a member (light guiding member) that has light guiding properties (light transmitting properties), for example, a fiber optic plate (FOP). Other than the FOP, a columnar crystal of CsI, or CsI doped with Tl (CsI:Tl), or the like may be used for the light guiding member of the structure 123.

An opening 123a is formed for each photoelectric conversion element 112 in the structure 123 as a through-hole positioned to be above the photoelectric conversion element 112. The opening 123a has an inner wall surface that is substantially vertical, and is smaller in areal dimensions than an opening of each photoelectric conversion element 112. The thickness of the structure 123 is set to 1,000 µm or less, for example, about 100 µm, in order to reduce light loss in light guiding. The scintillator layer 121 is formed on the structure 123 while filling the inside of the opening 123a. Forming the structure 123 enables the imaging apparatus 100 to guide light emitted on the radiation incident side toward the sensor panel 110, with the loss and diffusion of the light minimized.

The wavelength converting layer 120 in this embodiment has light transmitting properties in regions positioned to be above the plurality of photoelectric conversion elements 112 (regions above the plurality of photoelectric conversion elements 112 in each of which the scintillator layer 121 takes up the central portion and the structure 123 is present in a peripheral portion surrounding the central portion). The presence of the structure 123 makes the density of the scintillator layer 121 lower on the bottom side of the wavelength converting layer 120 than on the top side of the wavelength converting layer 120 opposite from the bottom side in the thickness direction of those regions. The scintillator layer 121 is formed thick (for example, about 200 µm or more, in this embodiment, about 350 µm) in order to secure a high DQE. With the structure 123 which has excellent light guiding properties formed in a lower part of the wavelength converting layer 120, light emitted by the scintillator layer 121 is guided toward the sensor panel 110 in those regions before absorbed. This shortens the light path length of light that passes through the scintillator layer 121 and arrives at the sensor panel 110, thereby reducing the absorption of light by the scintillator layer 121 and decreasing the attenuation of the amount of light. A sufficient amount of light enters the plurality of photoelectric conversion elements 112 as a result. In addition, with the structure 123 separating the plurality of photoelectric conversion elements 112 that are adjacent to each other, the diffusion of light between the adjacent photoelectric conversion elements 112 is reduced and an image high in sharpness is obtained.

The reflective layer 122 is a member for reflecting light, which has been converted from radiation by the scintillator layer 121 and which is traveling in a direction opposite from the plurality of photoelectric conversion elements 112, toward the photoelectric conversion elements 112. Forming the reflective layer 122 on the scintillator layer 121 improves sensitivity. The reflective layer 122 also has a function of preventing light that is not the one generated by the scintillator layer 121 (external light) from entering the plurality of photoelectric conversion elements 112.

A method of forming the wavelength converting layer 120 is described below. First, the structure 123 is formed on the sensor panel 110. The structure 123 is formed by first bonding a fiber optic plate (FOP), for example, to the top surface of the sensor panel 110 via the bonding member 130. The FOP is ground down to a desired thickness. A dry film resist is formed on the surface of the FOP and processed by lithography to form a mask pattern. Thereafter, the opening 123a, which is a through-hole, is formed in the FOP by, for example, reactive ion etching. The structure 123 partitioned by the opening 123a is formed in this manner.

Instead of etching, sand blasting in which fine ceramic particles are sprayed may be used to form the opening 123a in the FOP. The opening 123a may also be formed by machining such as five-axis milling.

The scintillator layer 121 is then formed on the structure 123 so that the inside of the opening 123a is filled. The scintillator that is a constituent of the scintillator layer 121 is, for example, gadolinium sulfide doped with a minute amount of terbium (Tb) (GOS:Tb). The scintillator used in the scintillator layer 121 can be a metal oxysulfide expressed by a general formula $Me_2O_2S:Re$ from the viewpoints of moisture resistance, light emission efficiency, heat process resistance, and light persistence properties. In this formula, Me is one selected from the group consisting of La, Y, and Gd, and Re is at least one selected from the group consisting of Tb, Sm, Eu, Ce, Pr, and Tm.

A binder that is a constituent of the scintillator layer 121 can be one that is dissolvable in an organic solvent and that has thixotropic characteristics. The binder may be specifically formed of a cellulose-based resin such as ethylcellulose or nitrocellulose, an acrylic resin such as polymethyl methacrylate, a polyvinyl acetal-based resin such as polyvinyl butyral solvent-based grade, or an epoxy resin. In addition, the binder may be formed of two or more kinds of those resins.

To form the scintillator layer 121, a scintillator solution is obtained first by mixing a scintillator material with a solvent, or mixing a scintillator material with a liquid adhesive. In the case where air bubbles are unwantedly mixed in the scintillator solution in this mixing step, defoaming treatment is performed with the use of a centrifugal defoaming machine or the like after the mixing. The scintillator solution is applied onto the structure 123 (the FOP having the opening 123a formed therein) to fill the inside of the opening 123a. The scintillator solution is applied by spin coating, slit coating, print coating, bar coating, doctor-blade, dipping, a marking apparatus, a dispenser, a brush, a flat paint brush, or the like. The scintillator layer 121 is formed in this manner.

The reflective layer 122 is then formed on the scintillator layer 121. The material of the reflective layer 122 is, for example, one of Al, stainless steel, Mg, Cu, Zn, Sn, Ti, and Mo, or an oxide or alloy of those elements, amorphous carbon, a carbon fiber reinforced material, or a molded resin product using an organic polymer. The reflective layer 122 is formed by bonding the above-mentioned material to the top surface of the scintillator layer 121 via a bonding layer. The reflective layer 122 may also be formed by depositing the above-mentioned material on the scintillator layer 121.

The wavelength converting layer 120 is obtained in the manner described above. Heat treatment may be performed on the wavelength converting layer 120 if necessary. The heat treatment removes the unnecessary solvent component in the scintillator solution, or cures the bonding member. The air bubbles mixed in the mixing step and the application step described above are removed by the heat treatment as well.

The sensor panel 110 and the wavelength converting layer 120 are bonded to each other by the bonding member 130. Instead of using the bonding member 130, the binder that is a constituent of the scintillator layer 121 may double as a bonding layer.

As has been described, the proportion and amount of light emitted by the scintillator layer 121 that enters the photoelectric conversion elements 112 formed immediately below the scintillator layer 121 are increased according to this embodiment, despite the scintillator layer 121 being formed thick. The imaging apparatus 100 that is high in the sharpness of a picked up image and excellent in DQE is thus realized.

MODIFICATION EXAMPLES

Modification examples of the first embodiment are described below. The modification examples in which radiographic imaging apparatuses are disclosed as in the first embodiment differ from the first embodiment in the shape of the structure formed in the wavelength converting layer.

Modification Example 1

Figure 3:
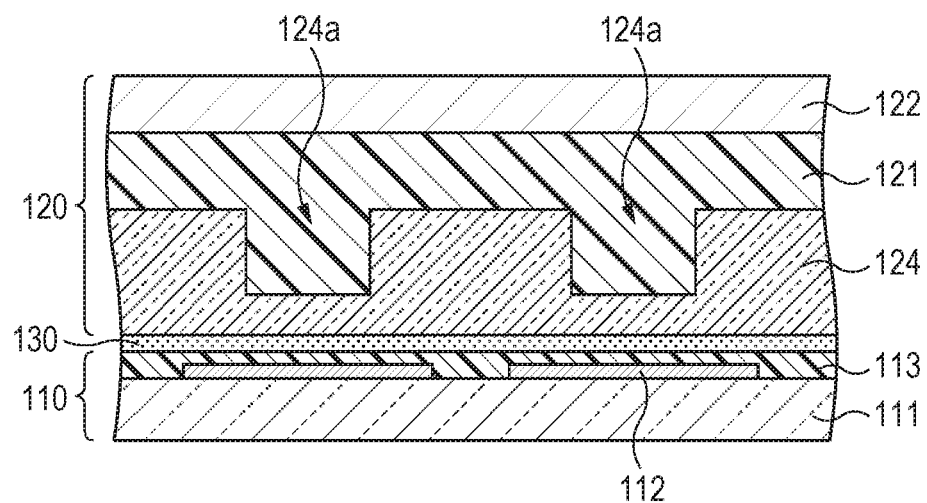
FIG. 3 is a schematic sectional view of the configuration of a radiographic imaging apparatus according to Modification Example 1 of the first embodiment.

FIG. 3 is a schematic sectional view of the configuration of a radiographic imaging apparatus according to Modification Example 1 of the first embodiment. Components that are the same as those in FIG. 2, which is referred to in the description of the first embodiment, are denoted by the same reference symbols that are used in FIG. 2, and detailed descriptions thereof are omitted. The wavelength converting layer 120 in the imaging apparatus 100 of FIG. 3 includes, in addition to the scintillator layer 121, the reflective layer 122 configured to reflect light of the scintillator layer 121 and a structure 124, which is a member having a function of guiding light emitted by the scintillator layer 121 toward the photoelectric conversion elements 112.

The structure 124 is formed from, for example, an FOP and has an opening 124a, which is formed for each photoelectric conversion element 112 as a non-through-hole positioned to be above the photoelectric conversion element 112. The opening 124a has an inner wall surface that is substantially vertical, and is smaller in areal dimensions than an opening of each photoelectric conversion element 112. The thickness of the structure 124 is set to 1,000 μm or less, for example, about 200 μm, in order to reduce light loss in light guiding. The scintillator layer 121 is formed on the structure 124 while filling the inside of the opening 124a.

Forming the structure 124 in the wavelength converting layer 120 enables the imaging apparatus 100 to guide light emitted on the radiation incident side toward the sensor panel 110, with the loss and diffusion of the light minimized. In Modification Example 1 where the opening 124a of the structure 124 is formed as a non-through-hole, the wavelength converting layer 120 can be bonded to the sensor panel 110 via the bonding member 130 after the wavelength converting layer 120 is formed from the structure 124, the scintillator layer 121, and the reflective layer 122.

As has been described, the proportion and amount of light emitted by the scintillator layer 121 that enters the photoelectric conversion elements 112 formed immediately below the scintillator layer 121 are increased according to Modification Example 1, despite the scintillator layer 121 being formed thick. The imaging apparatus 100 that is high in the sharpness of a picked up image and excellent in DQE is thus realized.

Modification Example 2

Figure 4:
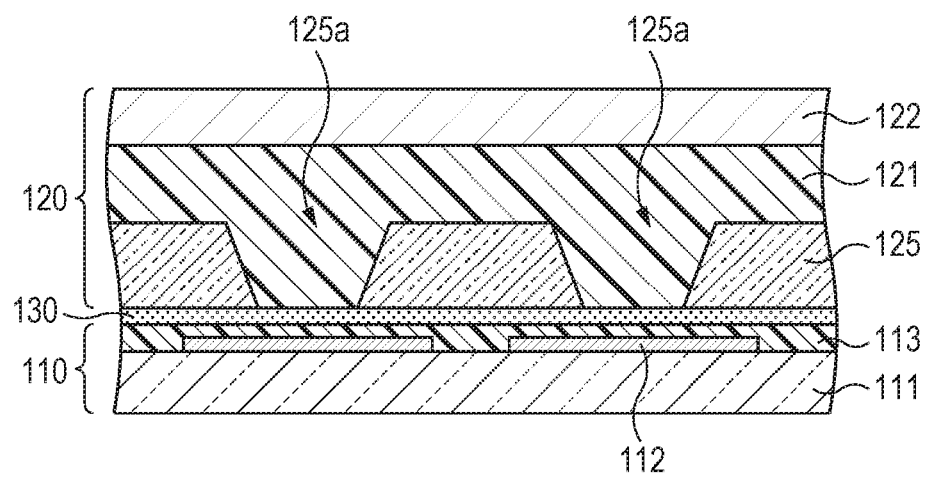
FIG. 4 is a schematic sectional view of the configuration of a radiographic imaging apparatus according to Modification Example 2 of the first embodiment.

FIG. 4 is a schematic sectional view of the configuration of a radiographic imaging apparatus according to Modification Example 2 of the first embodiment. Components that are the same as those in FIG. 2, which is referred to in the description of the first embodiment, are denoted by the same reference symbols that are used in FIG. 2, and detailed descriptions thereof are omitted. The wavelength converting layer 120 in the imaging apparatus 100 of FIG. 4 includes, in addition to the scintillator layer 121, the reflective layer 122 configured to reflect light of the scintillator layer 121 and a structure 125, which is a member having a function of guiding light emitted by the scintillator layer 121 toward the photoelectric conversion elements 112.

The structure 125 is formed from, for example, an FOP and has an opening 125a, which is formed for each photoelectric conversion element 112 as a through-hole positioned to be above the photoelectric conversion element 112. The thickness of the structure 125 is set to 1,000 μm or less, for example, about 100 μm, in order to reduce light loss in light guiding. The opening 125a has an inner wall surface that is tapered so that opening areal dimensions $S_1$ at the bottom end of the opening 125a (the sensor panel 110 side) are smaller than opening areal dimensions $S_2$ at the top end of the opening 125a (the radiation incident side) ($S_1 < S_2$). The opening areal dimensions $S_1$ are smaller than the opening areal dimensions of each photoelectric conversion element 112. As long as this relation of opening areal dimensions is satisfied, the inner wall surface of the opening 125a does not need to be linear in vertical section. The scintillator layer 121 is formed on the structure 125 while filling the inside of the opening 125a.

The thus structured wavelength converting layer 120 is capable of guiding light emitted on the radiation incident side toward the sensor panel 110 more efficiently. Forming the structure 125 enables the imaging apparatus 100 to guide light emitted on the radiation incident side toward the sensor panel 110, with the loss and diffusion of the light minimized.

Figure 5:
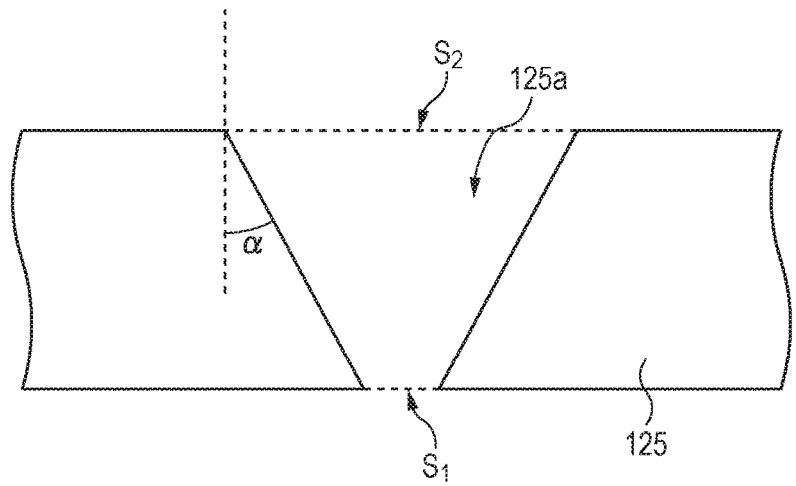
FIG. 5 is an enlarged schematic sectional view of a structure in Modification Example 2 of the first embodiment.

As illustrated in FIG. 5, a taper angle α of the opening 125a in the structure 125 is defined appropriately within a range of 0°<α<90° based on the thickness of the scintillator layer 121, the material of the scintillator layer 121, and other factors. The taper angle α in Modification Example 2 is about 23°, for example. The structure 125 is set to a thickness suited to the taper angle α.

As has been described, the proportion and amount of light emitted by the scintillator layer 121 that enters the photoelectric conversion elements 112 formed immediately below the scintillator layer 121 are increased according to Modification Example 2, despite the scintillator layer 121 being formed thick. The imaging apparatus 100 that is high in the sharpness of a picked up image and excellent in DQE is thus realized.

Modification Example 3

Figure 6:
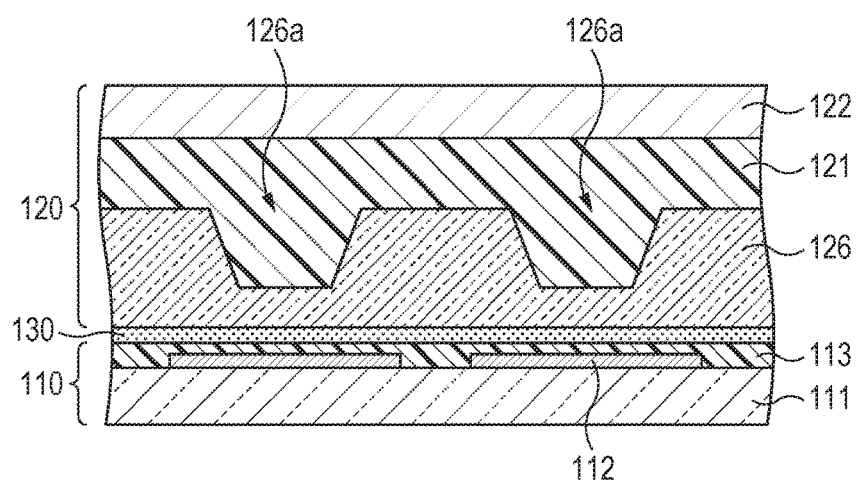
FIG. 6 is a schematic sectional view of the configuration of a radiographic imaging apparatus according to Modification Example 3 of the first embodiment.

FIG. 6 is a schematic sectional view of the configuration of a radiographic imaging apparatus according to Modification Example 3 of the first embodiment. Components that are the same as those in FIG. 2, which is referred to in the description of the first embodiment, are denoted by the same reference symbols that are used in FIG. 2, and detailed descriptions thereof are omitted. The wavelength converting layer 120 in the imaging apparatus 100 of FIG. 6 includes, in addition to the scintillator layer 121, the reflective layer 122 configured to reflect light of the scintillator layer 121 and a structure 126, which is a member having a function of guiding light emitted by the scintillator layer 121 toward the photoelectric conversion elements 112.

The structure 126 is formed from, for example, an FOP and has an opening 126a, which is formed for each photoelectric conversion element 112 as a non-through-hole positioned to be above the photoelectric conversion element 112. The thickness of the structure 126 is set to 1,000 μm or less, for example, about 200 μm, in order to reduce light loss in light guiding. The opening 126a has an inner wall surface that is tapered so that opening areal dimensions $S_1$ at the bottom end of the opening 126a (the sensor panel 110 side) are smaller than opening areal dimensions $S_2$ at the top end of the opening 126a (the radiation incident side) ($S_1<S_2$). The opening areal dimensions $S_1$ are smaller than the opening areal dimensions of each photoelectric conversion element 112. As long as this relation of opening areal dimensions is satisfied, the inner wall surface of the opening 126a does not need to be linear in vertical section. A taper angle α of the opening 126a is set to a value within a range of 0°<α<90°, for example, about 23°. The scintillator layer 121 is formed on the structure 126 while filling the inside of the opening 126a.

The thus structured wavelength converting layer 120 is capable of guiding light emitted on the radiation incident side toward the sensor panel 110 more efficiently. Forming the structure 126 enables the imaging apparatus 100 to guide light emitted on the radiation incident side toward the sensor panel 110, with the loss and diffusion of the light minimized.

In Modification Example 3 where the opening 126a of the structure 126 is formed as a non-through-hole, the wavelength converting layer 120 can be bonded to the sensor panel 110 via the bonding member 130 after the wavelength converting layer 120 is formed from the structure 126, the scintillator layer 121, and the reflective layer 122.

As has been described, the proportion and amount of light emitted by the scintillator layer 121 that enters the photoelectric conversion elements 112 formed immediately below the scintillator layer 121 are increased according to Modification Example 3, despite the scintillator layer 121 being formed thick. The imaging apparatus 100 that is high in the sharpness of a picked up image and excellent in DQE is thus realized.

Second Embodiment

Figure 7:
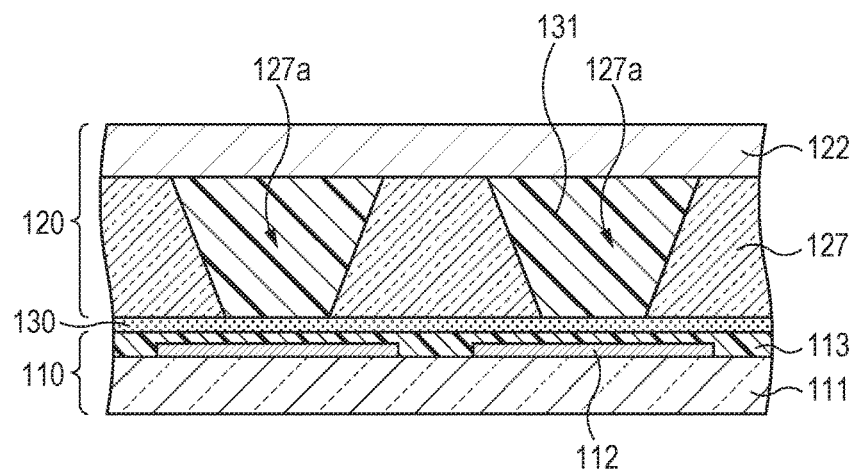
FIG. 7 is a schematic sectional view of the configuration of a radiographic imaging apparatus according to a second embodiment of the present invention.

A radiographic imaging apparatus is disclosed in a second embodiment of the present invention as in the first embodiment. The second embodiment differs from the first embodiment in the configuration of the wavelength converting layer. FIG. 7 is a schematic sectional view of the configuration of the radiographic imaging apparatus according to the second embodiment. Components that are the same as those in FIG. 2, which is referred to in the description of the first embodiment, are denoted by the same reference symbols that are used in FIG. 2, and detailed descriptions thereof are omitted.

In the imaging apparatus 100 of FIG. 7, the wavelength converting layer 120 includes a scintillator layer 131, the reflective layer 122 configured to reflect light of the scintillator layer 131, and a structure 127, which is a member having a function of guiding light emitted by the scintillator layer 131 toward the photoelectric conversion elements 112.

The structure 127 is formed from, for example, an FOP and has an opening 127a, which is formed for each photoelectric conversion element 112 as a through-hole positioned to be above the photoelectric conversion element 112. The thickness of the structure 127 is set to 1,000 μm or less, for example, about 300 μm, in order to reduce light loss in light guiding. The opening 127a has an inner wall surface that is tapered so that opening areal dimensions $S_1$ at the bottom end of the opening 127a (the sensor panel 110 side) are smaller than opening areal dimensions $S_2$ at the top end of the opening 127a (the radiation incident side) ($S_1<S_2$). The opening areal dimensions $S_1$ are smaller than the opening areal dimensions of each photoelectric conversion element 112. As long as this relation of opening areal dimensions is satisfied, the inner wall surface of the opening 127a does not need to be linear in vertical section. The thus structured wavelength converting layer 120 is capable of guiding light emitted on the radiation incident side toward the sensor panel 110 more efficiently.

A taper angle α of the opening 127a in the structure 127 is defined appropriately within a range of 0°<α<90° based on the thickness of the scintillator layer 131, the material of the scintillator layer 131, and other factors. The taper angle α in this embodiment is about 8°, for example. The structure 127 is set to a thickness suited to the taper angle α.

The scintillator layer 131 is formed so as to fill the inside of the opening 127a in the structure 127, and is formed only inside the opening 127a and not on the top surface of the structure 127. The scintillator layer 131 therefore has substantially the same height (thickness) as the structure 127.

The thus structured wavelength converting layer 120 is capable of guiding light emitted on the radiation incident side toward the sensor panel 110 more efficiently. Forming the structure 127 enables the imaging apparatus 100 to guide light emitted on the radiation incident side toward the sensor panel 110, with the loss and diffusion of the light minimized. In addition, forming the scintillator layer 131 only inside the opening 127a of the structure 127 further reduces the diffusion of light emitted by the scintillator layer 131 from one photoelectric conversion element 112 to its adjacent photoelectric conversion element 112, and the resultant imaging apparatus 100 is enhanced even more in the sharpness of a picked up image.

As has been described, the proportion and amount of light emitted by the scintillator layer 131 that enters the photoelectric conversion elements 112 formed immediately below the scintillator layer 131 are increased according to this embodiment, despite the scintillator layer 131 being formed thick. The imaging apparatus 100 that is high in the sharpness of a picked up image and excellent in DQE is thus realized.

MODIFICATION EXAMPLE

Figure 8:
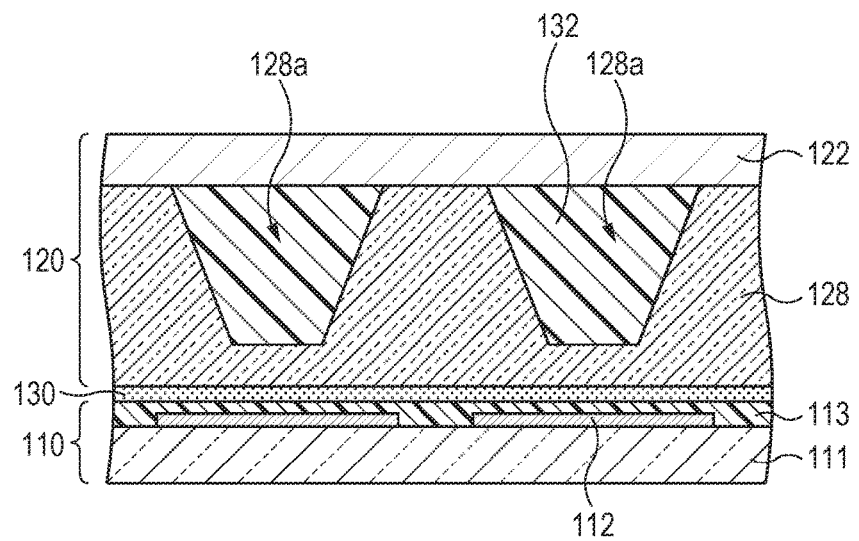
FIG. 8 is a schematic sectional view of the configuration of a radiographic imaging apparatus according to Modification Example of the second embodiment.

A modification example of the second embodiment is described below. The modification example in which a radiographic imaging apparatus is disclosed as in the second embodiment differs from the second embodiment in the shape of the structure formed in the wavelength converting layer. FIG. 8 is a schematic sectional view of the configuration of a radiographic imaging apparatus according to Modification Example of the second embodiment. Components that are the same as those in FIG. 7, which is referred to in the description of the second embodiment, are denoted by the same reference symbols that are used in FIG. 7, and detailed descriptions thereof are omitted.

In the imaging apparatus 100 of FIG. 8, the wavelength converting layer 120 includes a scintillator layer 132, the reflective layer 122 configured to reflect light of the scintillator layer 132, and a structure 128, which is a member having a function of guiding light emitted by the scintillator layer 132 toward the photoelectric conversion elements 112.

The structure 128 is formed from, for example, an FOP and has an opening 128a, which is formed for each photoelectric conversion element 112 as a non-through-hole positioned to be above the photoelectric conversion element 112. The thickness of the structure 128 is set to 1,000 μm or less, for example, about 300 μm, in order to reduce light loss in light guiding. The opening 128a has an inner wall surface that is tapered so that opening areal dimensions $S_1$ at the bottom end of the opening 128a (the sensor panel 110 side) are smaller than opening areal dimensions $S_2$ at the top end of the opening 128a (the radiation incident side) ($S_1 < S_2$). The opening areal dimensions $S_1$ are smaller than the opening areal dimensions of each photoelectric conversion element 112. As long as this relation of opening areal dimensions is satisfied, the inner wall surface of the opening 128a does not need to be linear in vertical section. A taper angle α of the opening 128a is set to a value within a range of $0° < α < 90°$, for example, about 8°.

The scintillator layer 132 is formed so as to fill the inside of the opening 128a, and is formed only inside the opening 128a and not on the top surface of the structure 128. The scintillator layer 132 therefore has substantially the same thickness as the structure 128.

The thus structured wavelength converting layer 120 is capable of guiding light emitted on the radiation incident side toward the sensor panel 110 more efficiently. Forming the structure 128 enables the imaging apparatus 100 to guide light emitted on the radiation incident side toward the sensor panel 110, with the loss and diffusion of the light minimized. In addition, forming the scintillator layer 132 only inside the opening 128a of the structure 128 further reduces the diffusion of light emitted by the scintillator layer 132 from one photoelectric conversion element 112 to its adjacent photoelectric conversion element 112, and the resultant imaging apparatus 100 is enhanced even more in the sharpness of a picked up image.

In this Modification Example where the opening 128a of the structure 128 is formed as a non-through-hole, the wavelength converting layer 120 can be bonded to the sensor panel 110 via the bonding member 130 after the wavelength converting layer 120 is formed from the structure 128, the scintillator layer 132, and the reflective layer 122.

As has been described, the proportion and amount of light emitted by the scintillator layer 132 that enters the photoelectric conversion elements 112 formed immediately below the scintillator layer 132 are increased according to this Modification Example, despite the scintillator layer 132 being formed thick. The imaging apparatus 100 that is high in the sharpness of a picked up image and excellent in DQE is thus realized.

Third Embodiment

Figure 9:
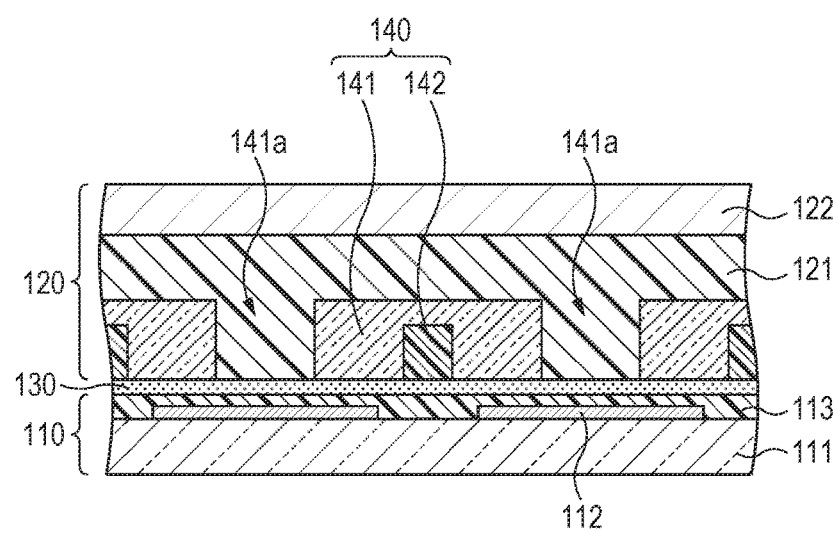
FIG. 9 is a schematic sectional view of the configuration of a radiographic imaging apparatus according to a third embodiment of the present invention.

A radiographic imaging apparatus is disclosed in a third embodiment of the present invention as in the first embodiment. The third embodiment differs from the first embodiment in the configuration of the structure in the wavelength converting layer. FIG. 9 is a schematic sectional view of the configuration of the radiographic imaging apparatus according to the third embodiment. Components that are the same as those in FIG. 2, which is referred to in the description of the first embodiment, are denoted by the same reference symbols that are used in FIG. 2, and detailed descriptions thereof are omitted.

In the imaging apparatus 100 of FIG. 9, the wavelength converting layer 120 includes the scintillator layer 121, the reflective layer 122 configured to reflect light of the scintillator layer 121, and a structure 140, which is a member having a function of guiding light emitted by the scintillator layer 121 toward the photoelectric conversion elements 112.

The structure 140 includes a first member 141, which is a part of the structure 140 and which has light transmitting properties, and a second member 142, which is covered with and contained inside the first member 141 to serve as a partition wall.

The first member 141 is a member that has light transmitting properties. The material of the first member 141 is high in light transmitting properties and low in light absorption, for example, a glass material or a light transmissive resin (acrylic resin or the like). The first member 141 may be hollow (with air or the like inside). The first member 141 may also be formed from a combination of different types of materials that are selected out of the materials given above.

The material of the second member 142 is lower in light transmitting properties than the first member 141, for example, a silicon wafer or an epoxy resin. The second member 142 can be formed from a reflective resin (for example, a resin containing a white pigment that is one type or two or more types selected from the group consisting of magnesium sulfate, magnesium carbonate, calcium carbonate, and titanium dioxide). A light transmissive material can also have the function of the second member 142 if surfaces of the material are covered with a thin metal film (for example, a thin film of one of Al, Au, Ag, Pt, Mg, Cu, Zn, Sn, Ti, and Mo, or a thin film of an oxide or alloy of those elements) by vapor deposition, sputtering, or the like. The metal thin film is effective also for the material of the second member 142 that is not reflective.

In the first member 141, an opening 141a is formed for each photoelectric conversion element 112 as a through-hole positioned to be above the photoelectric conversion element 112. The opening 141a has an inner wall surface that is substantially vertical, and is smaller in areal dimensions than an opening of each photoelectric conversion element 112. The opening 141a may have an inner wall surface that is tapered so that opening areal dimensions $S_1$ at the bottom end of the opening 141a (the sensor panel 110 side) are smaller than opening areal dimensions $S_2$ at the top end of the opening 141a (the radiation incident side) ($S_1<S_2$). The thickness of the first member 141 is set to 1,000 µm or less, for example, about 100 µm, in order to reduce light loss in light guiding. The scintillator layer 121 is formed on the structure 140 while filling the inside of the opening 141a of the first member 141.

The second member 142 is formed between the photoelectric conversion elements 112 that are adjacent to each other to serve as a partition wall by which each individual photoelectric conversion element 112 is sectioned off. The height (thickness) of the second member 142 is less than that of the first member 141, for example, about 80 µm.

Forming the structure 140 in the wavelength converting layer 120 enables the imaging apparatus 100 to guide light emitted on the radiation incident side toward the sensor panel 110, with the loss and diffusion of the light minimized. With the structure 140 formed from the first member 141 and the second member 142, high luminance is secured while maintaining the sharpness of a picked up image, despite the scintillator layer 121 being formed thick.

A method of forming the wavelength converting layer 120 is described below. The second member 142 of the structure 140 is formed first on the sensor panel 110. For example, a silicon wafer is used as a plate material and is bonded to the top surface of the sensor panel 110 via the bonding member 130. The silicon wafer is ground down to a desired thickness (for example, 80 µm). A resist pattern corresponding to the shape of partitioned sections is formed on the ground silicon wafer to be used as a mask for the etching of the silicon wafer. The second member 142 is formed in this manner between the photoelectric conversion elements 112 that are adjacent to each other.

The first member 141 of the structure 140 is then formed. For example, a light transmissive resin (acrylic resin or the like) is applied so as to cover the second member 142 and cured. A resist is applied to the cured light transmissive resin and is processed by lithography to form a mask pattern. The light transmissive resin is then etched to form the opening 141a, which is a through-hole. The opening areal dimensions of the opening 141a are, for example, approximately 50% of the opening areal dimensions of each photoelectric conversion element 112. The first member 141, which covers and contains the second member 142, is formed in this manner. The first member 141 and the second member 142 constitute the structure 140.

The scintillator layer 121 is then formed on the structure 140 so as to fill the inside of the opening 141a. The inside of the opening 141a is filled by applying a scintillator solution onto the first member 141 (a coat of a light transmissive resin having the opening 141a formed therein) as in the first embodiment. The scintillator layer 121 is formed in this manner.

The reflective layer 122 is then formed on the scintillator layer 121. The material of the reflective layer 122 is bonded to the top surface of the scintillator layer 121 via a bonding layer as in the first embodiment. The wavelength converting layer 120 is thus obtained.

As has been described, the proportion and amount of light emitted by the scintillator layer 121 that enters the photoelectric conversion elements 112 formed immediately below the scintillator layer 121 are increased according to this embodiment, despite the scintillator layer 121 being formed thick. The imaging apparatus 100 that is high in the sharpness of a picked up image and excellent in DQE is thus realized.

MODIFICATION EXAMPLES

Modification examples of the third embodiment are described below. The modification examples in which radiographic imaging apparatuses are disclosed as in the third embodiment differ from the third embodiment in the shape of the structure formed in the wavelength converting layer.

Modification Example 1

Figure 10:
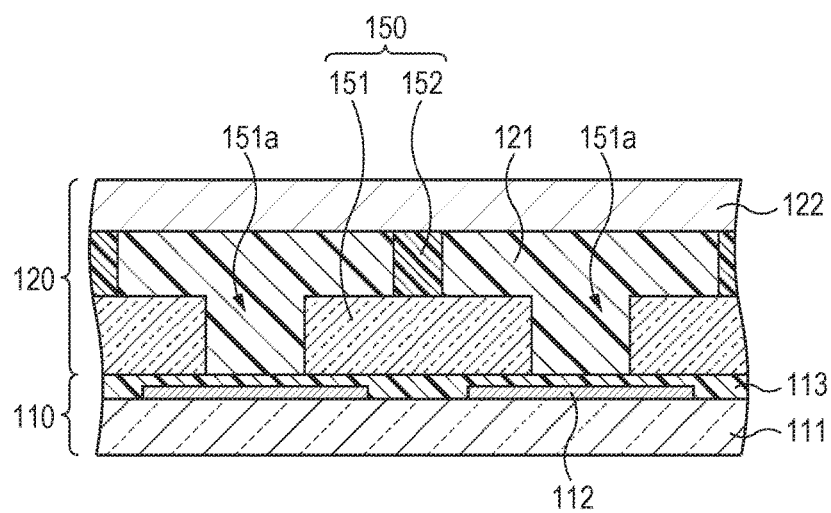
FIG. 10 is a schematic sectional view of the configuration of a radiographic imaging apparatus according to Modification Example 1 of the third embodiment.

FIG. 10 is a schematic sectional view of the configuration of a radiographic imaging apparatus according to Modification Example 1 of the third embodiment. Components that are the same as those in FIG. 9, which is referred to in the description of the third embodiment, are denoted by the same reference symbols that are used in FIG. 9, and detailed descriptions thereof are omitted. The wavelength converting layer 120 in the imaging apparatus 100 of FIG. 10 includes, in addition to the scintillator layer 121, the reflective layer 122 configured to reflect light of the scintillator layer 121 and a structure 150, which is a member having a function of guiding light emitted by the scintillator layer 121 toward the photoelectric conversion elements 112.

The structure 150 includes a first member 151 and a second member 152 formed on the first member 151.

The first member 151 is, as is the first member 141 in the third embodiment, formed from a material that is high in light transmitting properties and low in light absorption, for example, a glass material or a light transmissive resin. The second member 152 is, as is the second member 142 in the third embodiment, formed from a material that is lower in light transmitting properties than the first member 151, for example, a silicon wafer or an epoxy resin, from a reflective resin, from a light transmissive material of which surfaces are covered with a thin metal film, or from other materials.

The first member 151 has an opening 151a, which is formed for each photoelectric conversion element 112 as a through-hole positioned to be above the photoelectric conversion element 112. The opening 151a has an inner wall surface that is substantially vertical, and is smaller in areal dimensions than an opening of each photoelectric conversion element 112. The opening 151a may have an inner wall surface that is tapered so that opening areal dimensions $S_1$ at the bottom end of the opening 151a (the sensor panel 110 side) are smaller than opening areal dimensions $S_2$ at the top end of the opening 151a (the radiation incident side) ($S_1<S_2$). The thickness of the first member 151 is set to 1,000 µm or less, for example, about 100 µm, in order to reduce light loss in light guiding.

The second member 152 is formed between the photoelectric conversion elements 112 to serve as a partition wall by which each individual photoelectric conversion element 112 is sectioned off. The second member 152 is formed so as to be sandwiched between the top surface of the first member 151 and the bottom surface of the reflective layer 122. The scintillator layer 121 is formed so as to fill the inside of the opening 151a of the first member 151, and a region above the opening 151a between one second member 152 and another.

Forming the structure 150 in the wavelength converting layer 120 enables the imaging apparatus 100 to guide light emitted on the radiation incident side toward the sensor panel 110, with the loss and diffusion of the light minimized. With the structure 150 formed from the first member 151 and the second member 152 formed on the first member 151, high luminance is secured while maintaining the sharpness of a picked up image, despite the scintillator layer 121 being formed thick.

The structure 150 is formed as follows. The first member 151 of the structure 150 is formed first. For example, a light transmissive resin (acrylic resin or the like) is applied onto the sensor panel 110 and cured. A resist is applied to the cured light transmissive resin and is processed by lithography to form a mask pattern. The light transmissive resin is then etched to form the opening 151a, which is a through-hole. The opening areal dimensions of the opening 151a are, for example, approximately 50% of the opening areal dimensions of each photoelectric conversion element 112. The first member 151 is formed in this manner.

The second member 152 of the structure 150 is formed next. For example, a silicon wafer is bonded to the top surface of the first member 151, and is ground down to a desired thickness. A resist pattern corresponding to the shape of partitioned sections is formed on the ground silicon wafer in order to be used as a mask for the etching of the silicon wafer. The second member 152 is formed in this manner above a gap between the photoelectric conversion elements 112 that are adjacent to each other. Note that, the second member 152 may be formed after the surface of the material of the first member 151 is planarized before the opening 151a is formed. The structure 150 is thus formed from the first member 151 and the second member 152.

As has been described, the proportion and amount of light emitted by the scintillator layer 121 that enters the photoelectric conversion elements 112 formed immediately below the scintillator layer 121 are increased according to Modification Example 1, despite the scintillator layer 121 being formed thick. The imaging apparatus 100 that is high in the sharpness of a picked up image and excellent in DQE is thus realized.

Modification Example 2

Figure 11:
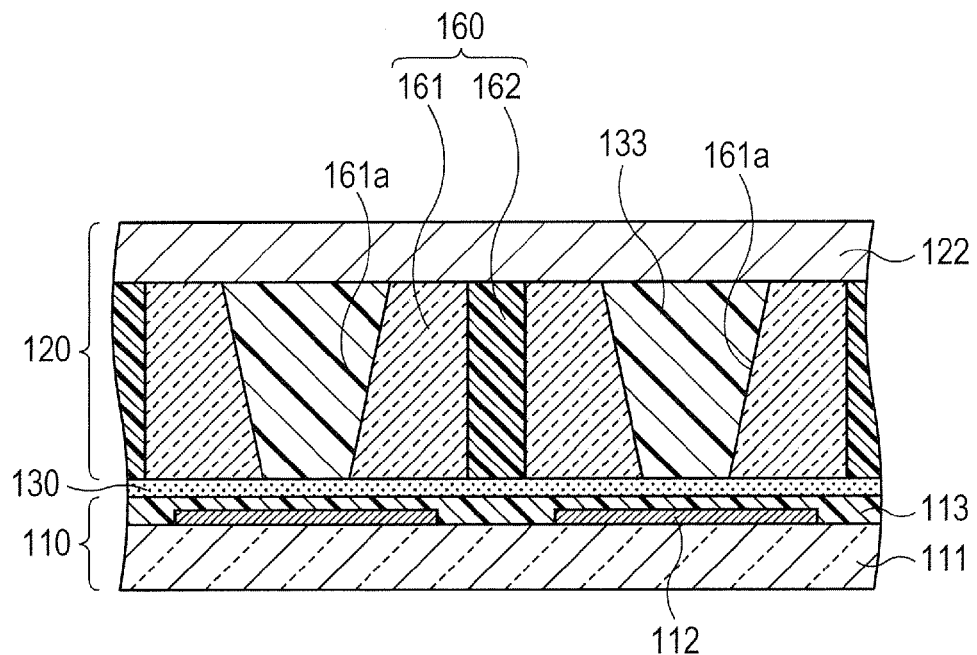
FIG. 11 is a schematic sectional view of the configuration of a radiographic imaging apparatus according to Modification Example 2 of the third embodiment.

FIG. 11 is a schematic sectional view of the configuration of a radiographic imaging apparatus according to Modification Example 2 of the third embodiment. Components that are the same as those in FIG. 9, which is referred to in the description of the third embodiment, are denoted by the same reference symbols that are used in FIG. 9, and detailed descriptions thereof are omitted. The wavelength converting layer 120 in the imaging apparatus 100 of FIG. 11 includes a scintillator layer 133, the reflective layer 122 configured to reflect light of the scintillator layer 133 and a structure 160, which is a member having a function of guiding light emitted by the scintillator layer 133 toward the photoelectric conversion elements 112.

The structure 160 includes a first member 161 and a second member 162, which separates one first member 161 and another first member 161 that are adjacent to each other.

The first member 161 is, as is the first member 141 in the third embodiment, formed from a material that is high in light transmitting properties and low in light absorption, for example, a glass material or a light transmissive resin. The second member 162 is, as is the second member 142 in the third embodiment, formed from a material that is lower in light transmitting properties than the first member 161, for example, a silicon wafer or an epoxy resin, from a reflective resin, from a light transmissive material of which surfaces are covered with a thin metal film, or from other materials.

The first member 161 has an opening 161a, which is formed for each photoelectric conversion element 112 as a through-hole positioned to be above the photoelectric conversion element 112. The thickness of the first member 161 is set to 1,000 μm or less, for example, about 300 μm, in order to reduce light loss in light guiding. The opening 161a has an inner wall surface that is tapered so that opening areal dimensions $S_1$ at the bottom end of the opening 161a (the sensor panel 110 side) are smaller than opening areal dimensions $S_2$ at the top end of the opening 161a (the radiation incident side) ($S_1 < S_2$). The opening areal dimensions $S_1$ are smaller than the opening areal dimensions of each photoelectric conversion element 112. As long as this relation of opening areal dimensions is satisfied, the inner wall surface of the opening 161a does not need to be linear in vertical section. The thus structured wavelength converting layer 120 is capable of guiding light emitted on the radiation incident side toward the sensor panel 110 more efficiently.

A taper angle α of the opening 161a of the first member 161 is defined appropriately within a range of 0°<α<90° based on the thickness of the scintillator layer 133, the material of the scintillator layer 133, and other factors. The taper angle α in this modification example is about 8°, for example. The first member 161 is set to a thickness suited to the taper angle α.

The second member 162 is formed between the photoelectric conversion elements 112 to serve as a partition wall by which each individual photoelectric conversion element 112 is sectioned off. The second member 162 is formed so as to be sandwiched between the top surface of the sensor panel 110 and the bottom surface of the reflective layer 122. The scintillator layer 133 is formed so as to fill the inside of the opening 161a in the first member 161, and is formed only inside the opening 161a and not on the top surface of the structure 160. All of the first member 161, the second member 162, and the scintillator layer 133 substantially have the same height (thickness) in Modification Example 2.

Forming the structure 160 in the wavelength converting layer 120 enables the imaging apparatus 100 to guide light emitted on the radiation incident side toward the sensor panel 110, with the loss and diffusion of the light minimized. With the structure 160 formed from the first member 161 and the second member 162, which partitions off the first members 161 that are adjacent to each other, high luminance is secured while maintaining the sharpness of a picked up image, despite the scintillator layer 133 being formed thick.

The structure 160 is formed as follows. The second member 162 of the structure 160 is formed first. For example, a silicon wafer is used as a plate material and is bonded to the top surface of the sensor panel 110 via the bonding member 130. The silicon wafer is ground down to a desired thickness (for example, about 300 μm). A resist pattern corresponding to the shape of partitioned sections is formed on the ground silicon wafer in order to be used as a mask for the etching of the silicon wafer. The second member 162 is formed in this manner, which partitions off the photoelectric conversion elements 112 that are adjacent to each other.

The first member 161 of the structure 160 is then formed. For example, a liquid light transmissive resin (acrylic resin or the like) fills a region between one second member 162 and another second member 162 and is cured. After that, a surface of the cured light transmissive resin is ground down to substantially the same height as that of the second member 162. A resist is applied to the ground light transmissive resin and is processed by lithography to form a mask pattern. The light transmissive resin is then etched to form the opening 161*a*, which is a through-hole. The opening areal dimensions at the bottom end of the opening 161*a* (the sensor panel 110 side) are, for example, approximately 50% of the opening areal dimensions of each photoelectric conversion element 112. The first member 161, which fills the region between the second members 162, is formed in this manner. The first member 161 and the second member 162 constitute the structure 160.

As has been described, the proportion and amount of light emitted by the scintillator layer 133 that enters the photoelectric conversion elements 112 formed immediately below the scintillator layer 133 are increased according to Modification Example 2, despite the scintillator layer 133 being formed thick. The imaging apparatus 100 that is high in the sharpness of a picked up image and excellent in DQE is thus realized.

Modification Example 3

Figure 12:
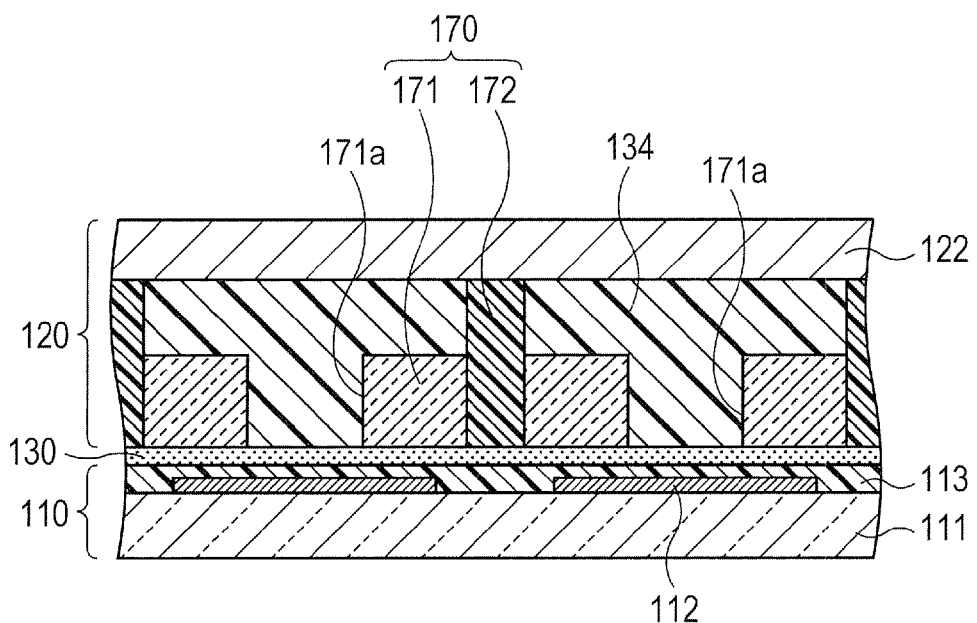
FIG. 12 is a schematic sectional view of the configuration of a radiographic imaging apparatus according to Modification Example 3 of the third embodiment.

FIG. 12 is a schematic sectional view of the configuration of a radiographic imaging apparatus according to Modification Example 3 of the third embodiment. Components that are the same as those in FIG. 9, which is referred to in the description of the third embodiment, are denoted by the same reference symbols that are used in FIG. 9, and detailed descriptions thereof are omitted. The wavelength converting layer 120 in the imaging apparatus 100 of FIG. 12 includes a scintillator layer 134, the reflective layer 122 configured to reflect light of the scintillator layer 134 and a structure 170, which is a member having a function of guiding light emitted by the scintillator layer 134 toward the photoelectric conversion elements 112.

The structure 170 includes a first member 171 and a second member 172, which partitions off the first members 171 that are adjacent to each other.

The first member 171 is, as is the first member 141 in the third embodiment, formed from a material that is high in light transmitting properties and low in light absorption, for example, a glass material or a light transmissive resin. The second member 172 is, as is the second member 142 in the third embodiment, formed from a material that is lower in light transmitting properties than the first member 171, for example, a silicon wafer or an epoxy resin, from a reflective resin, from a light transmissive material of which surfaces are covered with a thin metal film, or from other materials.

The first member 171 has an opening 171*a*, which is formed for each photoelectric conversion element 112 as a through-hole positioned to be above the photoelectric conversion element 112. The opening 171*a* has an inner wall surface that is substantially vertical, and is smaller in areal dimensions than an opening of each photoelectric conversion element 112. The opening 171*a* may have an inner wall surface that is tapered so that opening areal dimensions $S_1$ at the bottom end of the opening 171*a* (the sensor panel 110 side) are smaller than opening areal dimensions $S_2$ at the top end of the opening 171*a* (the radiation incident side) ($S_1 < S_2$). The thickness of the first member 171 is set to 1,000 μm or less, for example, about 100 μm, in order to reduce light loss in light guiding.

The second member 172 is formed between the photoelectric conversion elements 112 that are adjacent to each other to serve as a partition wall by which each individual photoelectric conversion element 112 is sectioned off. The second member 172 is formed so as to be sandwiched between the top surface of the sensor panel 110 and the bottom surface of the reflective layer 122. The height (thickness) of the second member 172 is more than that of the first member 171, for example, about 300 μm. In this modification example, the first member 171 is formed in a region between one second member 172 and another second member 172. The scintillator layer 134 is formed on the first member 171 while filling the inside of the opening 171*a* of the first member 171 in the region between one second member 172 and another second member 172. In other words, the region between one second member 172 and another second member 172 is filled with the first member 171 and the scintillator layer 134, and the second member 172 has substantially the same height (thickness) as the scintillator layer 134.

Forming the structure 170 in the wavelength converting layer 120 enables the imaging apparatus 100 to guide light emitted on the radiation incident side toward the sensor panel 110, with the loss and diffusion of the light minimized. With the structure 170 formed from the first member 171 and the second member 172, which partitions off the first members 171 that are adjacent to each other, high luminance is secured while maintaining the sharpness of a picked up image, despite the scintillator layer 134 being formed thick.

The structure 170 is formed as follows. The second member 172 is formed first to have a height (thickness) of about 300 μm by the same method that is used to form the second member 162 in Modification Example 2 of the third embodiment.

The first member 171 of the structure 170 is formed next. For example, a liquid light transmissive resin (acrylic resin or the like) is poured into a region between one second member 172 and another second member 172 until a given height (for example, about 100 μm) is reached, and cured. This may be accomplished by applying a minute amount of a light transmissive resin from above the second member 172 along the side wall surfaces of the second member 172, and then curing the resin. A resist is applied to the cured light transmissive resin and is processed by lithography to form a mask pattern. The light transmissive resin is then etched to form the opening 171*a*, which is a through-hole. The opening areal dimensions at the bottom end of the opening 171*a* (the sensor panel 110 side) are, for example, approximately 50% of the opening areal dimensions of each photoelectric conversion element 112. The first member 171, which fills the region between one second member 172 and another second member 172, is formed in this manner. The first member 171 and the second member 172 constitute the structure 170.

As has been described, the proportion and amount of light emitted by the scintillator layer 134 that enters the photoelectric conversion elements 112 formed immediately below the scintillator layer 134 are increased according to Modification Example 3, despite the scintillator layer 134 being formed thick. The imaging apparatus 100 that is high in the sharpness of a picked up image and excellent in DQE is thus realized.

Fourth Embodiment

Figure 13:
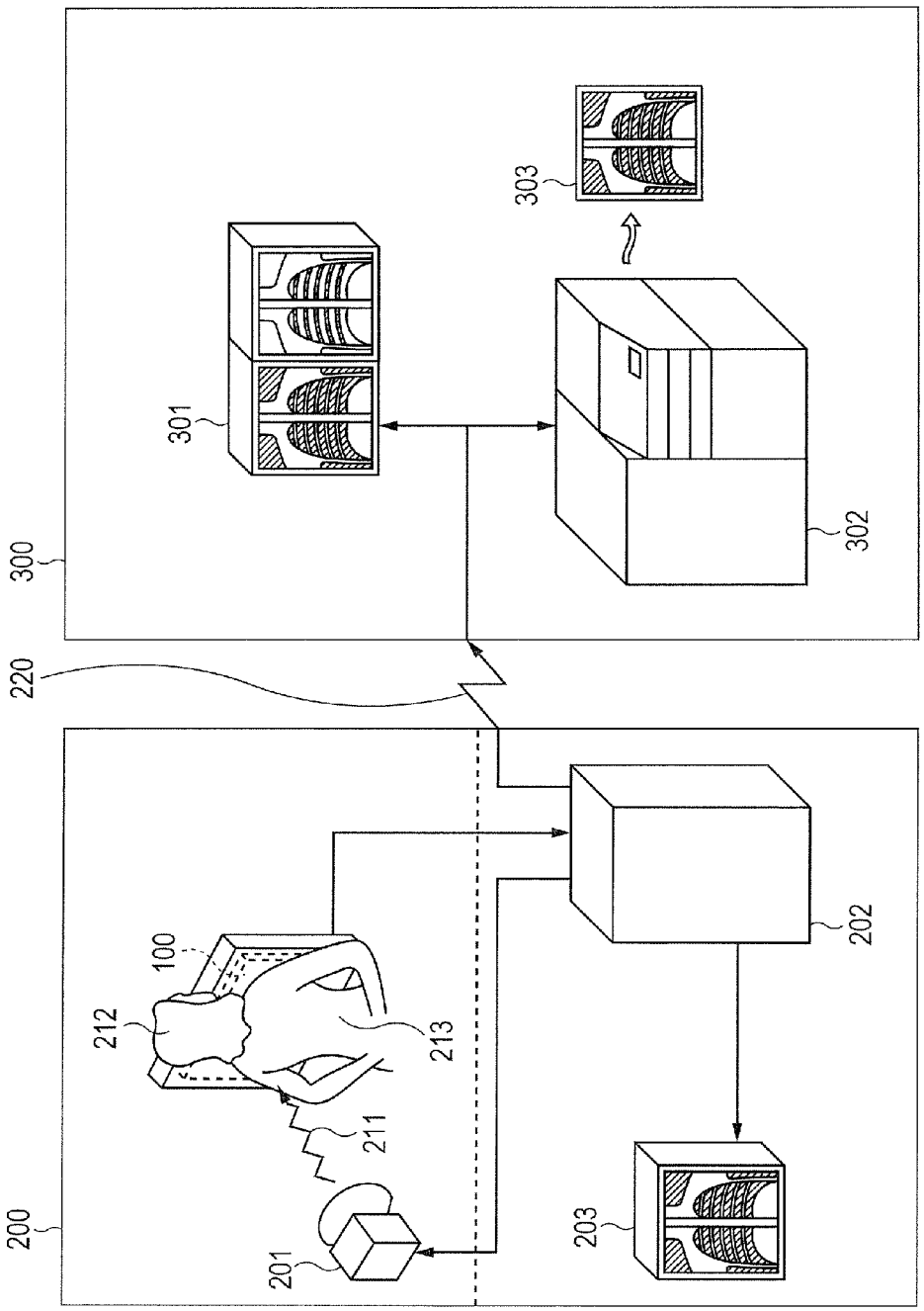
FIG. 13 is a schematic view for illustrating the schematic configuration of a radiographic imaging system according to a fourth embodiment of the present invention.

A fourth embodiment of the present invention gives an example of a radiographic imaging system, typically a radiographic examination apparatus, to which the imaging apparatus 100 of one of the first embodiment to the third embodiment is applied. FIG. 13 is a schematic view for illustrating the schematic configuration of a radiographic imaging system according to the fourth embodiment.

The radiographic imaging system is disposed in an X-ray room 200. The radiographic imaging system includes an X-ray tube 201, which is a radiation source for generating radiation, the imaging apparatus 100, a signal processing unit, which includes an image processor 202, and a display unit, which includes a display 203. The imaging apparatus 100 is one type of radiographic imaging apparatus selected from the first embodiment to the third embodiment (and the modification examples).

An X-ray 211 generated by the X-ray tube 201 is transmitted through a chest 213 of a subject 212 who is a patient or the like, and enters the imaging apparatus 100. The incident X-ray contains internal body information of the subject 212. The imaging apparatus 100 yields electrical information based on the incident X-ray 211. Thereafter, the electrical information is converted into digital information, which is subjected to image processing by the image processor 202 in order to be displayed on the display 203.

The electrical information is transferred to a remote site over a network 220, which is a telephone, a LAN, the Internet, or the like. The electrical information is thus displayed on a display 301 in another location such as a doctor room 300 so that a doctor on a remote site can make a diagnosis. The electrical information can be saved on, for example, an optical disc, and can also be recorded by a film processor 302 on a recording medium (storing unit) such as a film 303.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-206681, filed Oct. 7, 2014, which is hereby incorporated by reference herein in its entirety.

What is claimed is:

1. A radiographic imaging apparatus comprising:
a photoelectric conversion element;
a wavelength converting layer having a bottom surface located above the photoelectric conversion element, the wavelength converting layer comprising a scintillator layer, the scintillator layer comprising a scintillator to convert radiation into light; and
another photoelectric conversion element that is adjacent to the photoelectric conversion element,
wherein the wavelength converting layer has light transmitting properties in at least a region that is positioned to be above the photoelectric conversion element, and comprises a structure such that a density of the scintillator on a bottom surface side of the wavelength converting layer is lower than a density of the scintillator on a top surface side of the wavelength converting layer opposite from the bottom surface side in a thickness direction of the region,
wherein the structure has at least one part being transmissive of light and an opening positioned to be above the photoelectric conversion element and filled with the scintillator layer,
wherein the structure comprises:
a first member, which has the opening and which is transmissive of light; and
a second member, which is a partition wall formed between the photoelectric conversion element and the another photoelectric conversion element, and which is lower in light transmitting properties than the first member, and
wherein the structure is formed by arranging the second member on top of the first member.

2. The radiographic imaging apparatus according to claim 1, wherein the scintillator layer comprises a scintillator in a particle form, and the opening of the structure is smaller in areal dimensions at a bottom end than at a top end.

3. The radiographic imaging apparatus according to claim 2, wherein the scintillator layer is provided only inside the opening of the structure.

4. The radiographic imaging apparatus according to claim 2, wherein the opening of the structure comprises a through-hole.

5. The radiographic imaging apparatus according to claim 1, wherein the opening of the structure comprises a non-through-hole.

6. An imaging system comprising:
a radiation source arranged to generate radiation; and
a radiographic imaging apparatus according to claim 1.

* * * * *